United States Patent [19]

Coghlan et al.

[11] Patent Number: 5,296,484
[45] Date of Patent: Mar. 22, 1994

[54] QUINOLINE DERIVATIVES

[75] Inventors: Michael J. Coghlan, Indianapolis; Barry A. Dreikorn, Lawrence; Glen P. Jourdan, Morristown; Robert G. Suhr, Greenfield, all of Ind.

[73] Assignee: DowElanco, Indianapolis, Ind.

[21] Appl. No.: 325,734

[22] Filed: Mar. 20, 1989

Related U.S. Application Data

[63] Continuation-in-part of Ser. No. 150,103, Jan. 29, 1988, abandoned.

[51] Int. Cl.$^5$ ............... C07D 215/12; C07D 215/16; C07D 401/12; A01N 43/42
[52] U.S. Cl. ..................... 514/311; 514/63; 514/312; 514/313; 514/314; 546/14; 546/183; 546/153; 546/152; 546/159; 546/162; 546/171; 546/172; 546/174; 546/176; 546/177; 546/178; 546/181
[58] Field of Search ............ 546/153, 155, 156, 159, 546/162, 174, 14, 152, 171, 176, 181; 514/312, 259, 248, 63, 311, 312, 313; 544/283, 235, 284, 293, 187

[56] References Cited

U.S. PATENT DOCUMENTS

| | | | |
|---|---|---|---|
| 2,530,125 | 11/1950 | Kwartler et al. | 260/286 |
| 2,653,940 | 9/1953 | Johnson | 260/288 |
| 2,883,382 | 4/1959 | Elslager et al. | 544/283 |
| 3,075,981 | 1/1963 | Surrey | 260/256.4 |
| 3,075,984 | 1/1963 | Surrey | 260/288 |
| 3,184,462 | 5/1965 | Scarborough et al. | 544/283 |
| 3,248,292 | 4/1966 | Minielli et al. | 544/283 |
| 3,470,182 | 9/1969 | Sandoz . | |
| 3,541,094 | 11/1970 | Lutz et al. | 260/256.4 |
| 3,971,783 | 7/1976 | Barnish et al. | 260/256.4 |
| 4,213,987 | 7/1980 | Nakagami et al. | 424/251 |
| 4,236,912 | 12/1980 | Johnston et al. | 71/94 |
| 4,304,778 | 12/1981 | Nakagami et al. | 424/251 |
| 4,323,680 | 4/1982 | Nakagami et al. | 544/293 |
| 4,444,584 | 4/1984 | Serban et al. | 71/94 |
| 4,522,945 | 5/1985 | Vandenberk et al. | 514/259 |
| 4,551,474 | 11/1985 | Effland et al. | 514/309 |
| 4,657,916 | 4/1987 | Teranishi et al. | 514/312 |
| 4,829,069 | 5/1989 | Tahahashi et al. | 544/259 |
| 5,102,892 | 4/1992 | Geiss et al. | 546/159 |

FOREIGN PATENT DOCUMENTS

| | | | |
|---|---|---|---|
| 29319 | 5/1981 | European Pat. Off. | 544/283 |
| 0177764 | 4/1986 | European Pat. Off. . | |
| 0285089 | 10/1988 | European Pat. Off. | 544/283 |
| 322133 | 6/1989 | European Pat. Off. | 544/283 |
| 326330 | 8/1989 | European Pat. Off. | 544/283 |
| 39934 | 6/1965 | Fed. Rep. of Germany . | |
| 3028387 | 7/1980 | Fed. Rep. of Germany | 544/283 |
| 53-103484 | 9/1978 | Japan . | |
| 54-2325 | 1/1979 | Japan . | |
| 54-2326 | 1/1979 | Japan . | |
| 0002327 | 1/1979 | Japan | 514/259 |
| 54-2327 | 1/1979 | Japan . | |
| 55-76803 | 6/1980 | Japan . | |
| 67/6512 | 3/1968 | South Africa . | |
| 1233938 | 3/1971 | United Kingdom | 544/283 |
| 1364307 | 8/1974 | United Kingdom | 544/156 |
| 1496371 | 12/1977 | United Kingdom | C07D 215/42 |
| 2052481 | 5/1979 | United Kingdom | C07D 215/42 |
| 2043061 | 10/1980 | United Kingdom | 239/94/43/52 |
| 1598880 | 9/1981 | United Kingdom | 544/283 |
| 2135887 | 9/1984 | United Kingdom | 43/52/87/06 |
| 2185980 | 8/1987 | United Kingdom | A61K 31/13 |

OTHER PUBLICATIONS

Grant and Hackh's Chemical Dictionary (New York, McGraw-Hill Book Co., 1987) p.14.

(List continued on next page.)

Primary Examiner—John M. Ford
Attorney, Agent, or Firm—Donald R. Stuart

[57] ABSTRACT

The compounds of the formula:

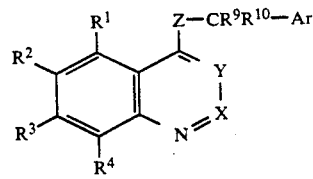

wherein the substituents are herein below defined; are plant fungicides, insecticides, and miticides.

24 Claims, No Drawings

OTHER PUBLICATIONS

Serafin et al., entry 948g; Chem. Abs. vol. 88:1 (1978).
Barnish et al., entry 31349t; Chem. Abs. vol. 82:5 (1975).
Fujimoto et al., entry 47321z; Chem. Abs. vol. 68:11 (1968).
Chem. Abs. 8th Collective Index vol's 66-75 Subj. Propane-Refo, 1967-1971, pp. 270, 428.
Schoenowsley et al., entry 182339a; Chem. Abs. vol. 97:21 (1982).
Schoenowsley et al., "Quirazelius: Their Prep. A Bio. Activity", Zeitschrifft Naturforsch. 37b, 907-911 (1962).
Derwent Abs, entry 87-025797/04 Kalien Pharm. v. Ltd., 76 1282-348A Jun. 8, 1985.
Derwent Abs. entry 74-66253v [38] DE 811856 Pfizer Corp.
Nakagami et al. (I), Translation J. P. Kalian 54-2325 [29-2325].
Nakagami et al., (II), Tranx J. P. Kalien 511-2327 [29-2327].
Nakagami et al. (III); Tranx J. P. Kalic, 54-2326 [79-2726].
Derwent Abstract, 66-33787 (abstracting JA 19548/68).
H. Gildemeister et al., *Leibigs. Ann. Chem.* 1982, vol 9 pp. 1656-76.
*Chem. Abstract*, 57:16760e (1962).
*J.A.C.S.*, 73:2623-26 (1951), Alexander R. Surrey & Royal A. Cutler, The Role of Phenol in the Reaction of 4,7-Dichloroquinoline with Novol Diamine.
*Arzneim-Forsch./Drug Research*, 32(II): 1219-23 (1982), Von O. Dann, W. Steuding, K. G. Lisson, H. R. Scidel, E. Fink, P. Nickel, Gegan Malaria wirksame 6-Aminochinoline.
*Eur. J. Med. Chem.-Chim. Ther.*, 21:5-8 (1986), Syed Abuzar, Rashmi Dubey, & Satyavan Sharma. Synthesis of some new 7-chloro-4-substituted quinolines as potential antiparasitic agents (1).
*Chem. Abst.*, 61:5600h (1964).
*Chem. Abst.*, 53:2229i (1959).
*Derwent Abst.*, 81-71882 (abstracting DE 3008813).
*Derwent Abst.*, 82-70390 (abstracting DE 3101544).
*Chem. Abst.*, 57:16552 (1962), abstracting Yakugaku Zasshi 82, 937-42 (1962).
A Survey of Antimalarial Drugs, vol. II, pp. 1046, 1117, 1120, 1124, 1127, 1151, 1153, 1154, 1214, 1246-1250, F. Y. Wiselogle, ed., (1946).

*Derwent Abst.*, 87-025797/04, abstracting J61282348a (published Dec. 12, 1986).
*Derwent Abst.*, 47262R-B, abstracting FR 182572.
*Derwent Abst.*, 56916C/33, abstracting BE 882414 (1980).
*Chem. Abst.*, 58:8254c (1963) abstracting *Ann. Biochem. Exptl. Med.* (Calcutta) Suppl. 20, 493-504 (1960).
*Chem. Abst.*, 55:1665g (1961), abstracting Ger. (East) 16,921 (1959).
*Derwent Abst.*, 86-015636/03, abstracting ES 8505515A.
*C. A. Selects: Novel Pesticides & Herbicides*, Issue 17 (1986), p. 5.
*Chem. Abst.*, 60:2914e (1964), abstracting FR.M1729.
*Derwent Abstract*, 86-171372/27, abstracting GB 2168977a.
*Chem. Abst.*, 98:50223u (1983), abstracting *Zentralbl. Pharm. Pharmakother Laboratoriumsdiagn*, 1982, 121 (19), 979-83.
*J. Med. Chem.*, 30, 1987 906-911, Stephen J. Kesten, Judith Johnson, & Leslie M. Werbel, Synthesis & Antimalarial Effects of 4-((7-Chloro-4-quinolinyl)amino)-2-((diethylamino)methyl)-6-alkylphenols & their $N^w$-Oxides [1,2].
J. A. 20294/68.
*Derwent Abst.*, 32, 452, abstracting BE 706,646 (1968).
Derwent Abst. 56916C/33, abstracting B. E. 882,414.
*Chem. Abst.*, 88:83971h (1978), abstracting *Ann. Pharm. Fr.*, 1977, 35 (7-8), 239-47.
*Derwent Abst.* 12729y/08, abstracting BE 845,271.
*Chem. Abst.*, 91:140694h (1979), abstracting *Atti. Accad. Sci. Sieng Fisiocrit.* 1976, 8, 43-57.
*Derwent Abst.*, 86:318826/48, abstracting WO 8606-72-1-A.
*Derwent Abst.*, 86-144574 abstracting DD 232700 to Akademie der Wissenschften.
*Derwent Abst.*, 66-32333F abstracting U.S. 3,385,856.
*Derwent Abst.*, 67-05579H, abstracting NL 6814057.
*Derwent Abst.*, 66-F41384, abstracting U.S. 3,483,200.
*Derwent Abst.*, 66-F33954, abstracting U.S. 3,403,153.
*Derwent Abst.*, 67-04302H, abstracting NL 6807380.
*Derwent Abst.*, 67-05394H, abstracting NL 6812978.
*Derwent Abst.*, 67-06714H, abstracting U.S. 3,454,573.
*J. Chem. Soc.* (B) 1967, p. 892.
*J. Chem. Soc. Perkin Transactions*, 1, 1975, pp. 2322-2326.

OTHER PUBLICATIONS

*Bull. de la Societe Chimique de France* 1963, pp. 1161-1166.

*Chemical and Pharmaceutical Bulletin* 32, p. 3690 (1984).

*Chemical and Pharmaceutical Bulletin* 33, p. 950 (1985).

*Chemie Therapeutique,* vol. 2, pp. 202-212 (1967).

Renault et al. Chemical Abstracts, vol. 69, 1968 Abstract 106507k.

Hayashi et al. Chemical Abstracts vol. 54, 1960 Abstract 22665.

Saneyoshi et al. Chem. Pharm. Bull. 16(7) 1390-1394 (1968).

Katkevich et al. Chemical Abstracts, vol. 104, 1986 Abstract 81530p.

Suyama et al., Chem. Abs. vol. 110 No. 5 entry #38746a (1989).

Hamana et al., Chem. Abs. vol. 70 No. 15 entry #68193r (1969).

Buchmann, Chem. Abs. vol. 57 entry 16760e.

Hoechst AG, Derwent Abs., entry 70390 E/34 CO2 (1981).

Chemical Abstract 86:140078g (1977).

Chemical Abstract 84:150043q (1976).

Chemical Abstract 94:156855 (1981).

Chemical Abstract 84:105533p (1976).

Chemical Abstract 68:103651w (1968).

Chemische Berichte, vol. 117, No. 4, Apr. 1984, pp. 1523-1536.

J. of Medicinal Chemistry, vol. 14, No. 4, Apr. 1971, pp. 283-286.

Chimie Therapeutique, Nos. 5-6, Jul.-Oct. 1966, pp. 339-346.

Bulletin De la Societe Chimique DE France, No. 1, Jan. 1971, pp. 211-214.

Bulletin De la Societe Chimiques DE France, No. 11, Nov. 1973, pp. 3175-3178.

Chemical Abstract 90:87501u.

Chemical Abstract 90:198860e.

Chemical Abstract 90:198861f.

Chemical Abstract 90:181579x.

Chemical Abstract 97:140302c.

QUINOLINE DERIVATIVES

RELATED APPLICATIONS

This application is a continuation-in-part of Ser. No. 07/150,103, filed Jan. 29, 1988, now abandoned.

BACKGROUND OF THE INVENTION

1. Field of the Invention

This invention provides new compounds that have excellent plant fungicide activity. Some of the compounds have also demonstrated insecticidal and miticidal activity. The invention also provides compositions and combination products that contain a compound of the invention as active ingredient. The invention also provides fungicidal, miticidal, and insecticidal methods.

There is an acute need for new fungicides, insecticides, and miticides, because target pathogens are rapidly developing resistance to currently used pesticides. Widespread failure of N-substituted azole fungicides to control barley mildew was observed in 1983, and has been attributed to the development of resistance. At least 50 species of fungi have developed resistance to the benzimidazole fungicides. The field performance of DMI (demethylation inhibitor) fungicides, which are now widely relied on to protect cereal crops from powdery mildew, has declined since they were introduced in the 1970's. Even recent fungicides, like the acylalanines, which initially exhibited excellent control of potato late blight and grape downy mildew in the field, have become less effective because of widespread resistance. Similarly, mites and insects are developing resistance to the miticides and insecticides in current use. Resistance to insecticides in arthropods is widespread, with at least 400 species resistant to one or more insecticides. The development of resistance to some of the older insecticides, such as DDT, the carbamates, and the organophosphates, is well known. But resistance has even developed to some of the newer pyrethroid insecticides and miticides. Therefore a need exists for new fungicides, insecticides, and miticides.

SUMMARY OF THE INVENTION

The fungicidal method of the invention comprises applying to the locus of a plant pathogen a disease inhibiting and phytologically acceptable amount of a compound of formula (1)

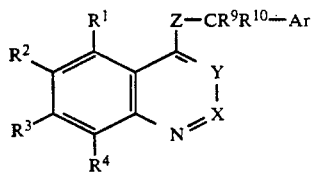

wherein
$R^1$ to $R^4$ are independently:
H, halo, I, ($C_1$-$C_4$) alkyl, branched ($C_3$-$C_4$) alkyl, halo ($C_1$-$C_4$) alkyl, $C_1$-$C_4$ alkoxy, halo ($C_1$-$C_4$) alkoxy, $NO_2$, or $NH_2$, at least two of $R^1$ to $R^4$ being H,
one of X and Y is N and the other is $CR^5$, or both X and Y are $CR^5$,
$R^5$ is H, $CH_3$, or Cl;
Z is O, $NR^6$, S, SO, $SO_2$, or $CR^7R^8$;
$R^6$ is H, ($C_1$-$C_4$) alkyl, or ($C_2$-$C_4$) acyl;
$R^7$ and $R^8$ are independently H, ($C_1$-$C_4$) alkyl, branched ($C_3$-$C_4$) alkyl, or ($C_1$-$C_4$) acyl, or $R^7$ and $R^8$ combine to form a saturated or unsaturated carbocyclic ring containing three to seven carbon atoms, or one or and $R^7$ can combine with one or both of $R^9$ and $R^{10}$ to form a multiple bond;
$R^9$ and $R^{10}$ are independently H, ($C_1$-$C_3$) alkyl, substituted phenyl, ($C_3$-$C_8$) cycloalkyl, hydroxy, halo, I, or acetyl, or $R^9$ and $R^{10}$ combine to form a saturated or unsaturated carbocyclic ring containing three to seven carbon atoms; and
Ar is ($C_3$-$C_8$) cycloalkyl,
substituted ($C_3$-$C_8$) cycloalkyl,
($C_3$-$C_8$) cycloalkenyl,
naphthyl,
substituted naphthyl,
dihydronaphthyl,
tetrahydronaphthyl,
decahydronaphthyl,
1,3-benzodioxolyl,
fluorenyl,
pyridyl,
substituted pyridyl,
2,3-dihydro-1,4-benzodioxin-2-yl,
furyl optionally substituted with halo, I, $CF_3$, CN, $NO_2$, ($C_1$-$C_4$) alkyl, branched ($C_3$-$C_4$) alkyl, phenyl, or ($C_1$-$C_4$) alkoxy,
thienyl optionally substituted with halo, I, $CF_3$, CN, $NO_2$, ($C_1$-$C_4$) alkyl, branched ($C_3$-$C_4$) alkyl, phenyl, or ($C_1$-$C_4$) alkoxy,
a group of the formula (2) or (2a)

wherein $R^{11}$ is H, halo, I, $CF_3$, CN, $NO_2$, ($C_1$-$C_4$) alkyl, branched ($C_3$-$C_4$) alkyl, phenyl, or ($C_1$-$C_4$) alkoxy, M is N or CH and G is O, $NR^{20}$, or $CH_2$, provided that M is N or G is $NR^{20}$, where $R^{20}$ is H, ($C_1$-$C_4$) alkyl, ($C_1$-$C_4$) acyl,
a group of the formula (3)

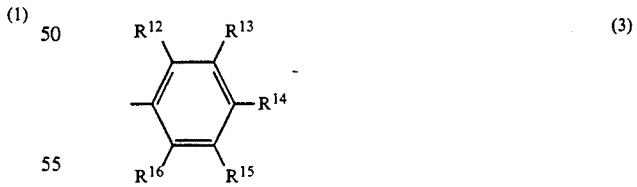

wherein
$R^{12}$ to $R^{16}$ are independently H, halo, I, ($C_1$-$C_{10}$) alkyl, branched ($C_3$-$C_6$) alkyl, halo ($C_1$-$C_7$) alkyl, ($C_1$-$C_7$) alkoxy, halo ($C_1$-$C_7$) alkoxy, phenoxy, substituted phenoxy, phenyl, substituted phenyl, phenylthio, or substituted phenylthio, $NO_2$, $NH_2$, acetoxy, OH, CN, or $SiR^{17}R^{18}R^{19}$, or $OSiR^{17}R^{18}R^{19}$, where $R^{17}$, $R^{18}$, and $R^{19}$ are independently $C_1$-$C_4$ alkyl, $C_1$-$C_4$ branched alkyl, phenyl, or substituted phenyl, provided that unless each of $R^{12}$ to $R^{16}$ is F, $CH_3$, or H, then at least two of $R^{12}$ to $R^{16}$ are H;

or an acid addition salt of a compound of formula (1), or an N-oxide of a compound of formula (1) where Y is $CR^5$;

provided that if $R^1$ to $R^4$ are all H, X is $CR^5$, Y is N, and Z is $NR^6$, then Ar is naphthyl or a group of formula (3) wherein one of $R^{12}$ to $R^{16}$ is phenyl, substituted phenyl, phenoxy, substituted phenoxy, phenylthio, or substituted phenylthio, halo $(C_1-C_4)$ alkyl, or halo $(C_1-C_4)$ alkoxy:

if $R^1$ to $R^4$ are all H, X is CH, and Y is N, then at least one of $R^9$ and $R^{10}$ is other than H; and Ar is not 5-nitro-2-furyl.

The fungicidal combinations of the invention comprise at least 1% by weight of a compound of formula (1) in combination with a second fungicidal compound.

The fungicidal compositions of the invention comprise a compound of the formula (1) in combination with a phytologically-acceptable carrier.

The invention provides compounds of formula (1) as described above, provided that (1) if X and Y are $CR^5$ and Z is $NR^6$, then $R^4$ is Cl or F, or Ar is a group of formula (3) wherein one of $R^{12}$ to $R^{16}$ is substituted phenyl, phenoxy, substituted phenoxy, phenylthio, or substituted phenylthio, halo $(C_1-C_4)$ alkyl, or halo $(C_1-C_4)$ alkoxy, (2) if $R^1$ to $R^4$ are all H, X is $CR^5$, Y is N, and Z is $NR^6$, then Ar is naphthyl or a group of formula (3) wherein one of $R^{12}$ to $R^{16}$ is phenyl, substituted phenyl, phenoxy, substituted phenoxy, phenylthio, or substituted phenylthio, halo $(C_1-C_4)$ alkyl, or halo $(C_1-C_4)$ alkoxy;

(3) if $R^1$ to $R^4$ are all H, X is CH, and Y is N, then at least one of $R^9$ and $R^{10}$ is other than H; and (4) Ar is not 5-nitro-2-furyl.

DETAILED DESCRIPTION OF THE INVENTION

Throughout this document, all temperatures are given in degrees Celsius, and all percentages are weight percentages unless otherwise stated.

The term "halo", used alone or in combination with other terms, refers to F, Cl, or Br, unless otherwise indicated.

The terms "$(C_1-C_3)$ alkyl", "$(C_1-C_4)$ alkyl", and "$(C_1-C_{10})$ alkyl" refer to straight chain alkyl radicals.

The terms "branched $(C_3-C_4)$ alkyl", and "branched $(C_3-C_6)$ alkyl" refer to all alkyl isomers containing the designated number of carbon atoms, except the straight chain isomers.

The term "$(C_1-C_7)$ alkoxy" refers to straight or branched chain alkoxy groups.

The term "halo $(C_1-C_7)$ alkyl" refers to a $(C_1-C_7)$ alkyl group, straight chain or branched, substituted with one or more halo atoms.

The term "halo $(C_1-C_7)$ alkoxy" refers to a $(C_1-C_7)$ alkoxy group, substituted with one or more halo atoms.

The term "$(C_1-C_4)$ acyl" refers to straight chain or branched acyl groups.

The term "substituted phenyl" refers to phenyl substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, phenoxy, phenyl, $NO_2$, OH, CN, $(C_1-C_4)$ alkanoyloxy, or benzyloxy.

The term "substituted phenoxy" refers to phenoxy substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "substituted phenylthio" refers to a phenylthio group substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "substituted phenylsulfonyl" refers to a phenylsulfonyl group substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1C_7)$ alkoxy, halo $(C_1-C_7)$ alkoxy, phenoxy, phenyl, $NO_2$, OH, CN, $(C_1-C_4)$ alkanoyloxy, or benzyloxy.

The term substituted $(C_3-C_8)$ cycloalkyl refers to a $(C_3-C_8)$ cycloalkyl group substituted with one or more halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, or benzyloxy groups.

The term "substituted pyridyl" refers to a pyridyl group substituted with halo, halomethyl, CN, $NO_2$, $(C_1-C_4)$ alkyl, $(C_3-C_4)$ branched alkyl, phenyl, $(C_1-C_7)$ alkoxy, or halo $(C_1-C_7)$ alkoxy.

The term "HPLC" refers to high-performance liquid chromatography.

COMPOUNDS

While all of the compounds of the invention are useful fungicides, certain classes are preferred for reasons of greater efficacy or ease of synthesis, viz:

1. compounds of formula (1) wherein X and Y are $CR^5$, i.e., substituted quinolines;
2. compounds of preferred class 1 wherein $R^9$ is $CH_3$ and $R^{10}$ is H;
3. compounds of preferred class 1 wherein Z is O, i.e., 4-quinolinyl ethers;
4. compounds of preferred class 3 wherein $R^3$ is Cl, i.e., 7-chloro-4-quinolinyl ethers;
5. compounds of preferred class 4 wherein Ar is a group of formula (3) wherein at least one of $R^{12}$ to $R^{16}$ is F;
6. compounds of preferred class 4 wherein Ar is a group of formula (3) wherein at least one of $R^{12}$ to $R^{16}$ is $CF_3$;
7. compounds of formula (1) wherein $R^4$ is F.
8. compounds of formula (1) wherein X is CH and Y is N, i.e., substituted quinazolines;
9. compounds of preferred class 8 wherein Z is O, i.e., 4-quinazolinyl ethers;
10. compounds of preferred class 9 wherein $R^9$ is $CH_3$ and $R^{10}$, is $CF_3$.
11. compounds of preferred class 8 wherein Z is $NR^6$ and Ar is a group of formula (3) wherein at least one of $R^{12}$ to $R^{16}$ is $CF_3$.

Compounds exhibiting particularly good activity against powdery mildew, including curative activity as well as protective activity, are:

7-chloro-4-[1-(2-fluorophenyl)ethoxy]quinoline
7-chloro-4-[1-(3-fluorophenyl)ethoxy]quinoline
7-chloro-4-[1-(4-fluorophenyl)ethoxy]quinoline
N-[[2-(trifluoromethyl)phenyl]methyl]-4-quinazolinamine
(S)-7-chloro-4-(1-(2-fluorophenyl)ethoxy)-quinoline
(R)-7-chloro-4-(1-(2-fluorophenyl)ethoxy)-quinoline.

Compounds exhibiting particularly good activity against downy mildew include:

N-[[3-(trifluoromethyl)phenyl]methyl]-4-quinazolinamine

N-[(4-chlorophenyl)methyl]-8-fluoro-4-quinolinamine

N-[1-(4-chlorophenyl)ethyl]-8-fluoro-4-quinolinamine

N-[[3-(trifluoromethyl)phenyl]methyl]-4-quinazolinamine exhibits particularly good activity against wheat leaf rust.

4-[1-[4-(1,1-dimethylethyl)phenyl]ethoxy]quinazoline exhibits particularly good activity against mites.

SYNTHESIS

The compounds of this invention are made using well known chemical procedures. The required starting materials are commercially available, or they are readily synthesized using standard procedures.

Synthesis of Compounds Wherein Z is O

The compounds of formula (1) wherein Z is O were made by condensing a compound of formula (4):

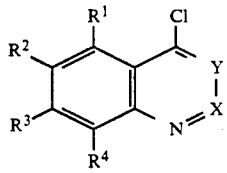

where $R^1$ to $R^4$, X and Y are as previously defined, with an alcohol of the formula (5):

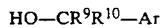

where $R^9$, $R^{10}$, and Ar are as previously defined.

The reaction is preferably carried out in the presence of a strong base, such as sodium hydride, in a non-reactive organic solvent, such as DMF, at a temperature in the range of 0° to 160° C.

This reaction proceeds with retention of configuration, a fact which can be significant when an optically active starting material of formula (5) is used.

Alternatively, compounds of formula (1) wherein Z is O can be prepared by reacting a compound of formula (7)

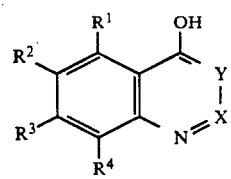

where $R^1$ to $R^4$, X, and Y are as previously defined, with a compound of formula (5)

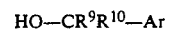

using the diethyl azodicarboxylate/triphenylphosphine (DEAD/PPh$_3$) reaction, as described, for example, in *Synthesis*, 1 (1981). The reaction is carried out in an aprotic solvent. One to 1.5 equivalents each of DEAD and PPh$_3$ are used, and the reaction is carried out at room temperature or below. This reaction proceeds with inversion of configuration.

Synthesis of Compounds Wherein Z is NR$^6$

The compounds of formula (1) wherein Z is NR$^6$ were prepared by condensing a compound of formula (4) with an amine of the formula (6)

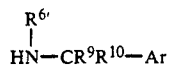

where $R^{6'}$ is H or (C$_1$-C$_4$) alkyl, and $R^9$, $R^{10}$, and Ar are as previously defined. The chloride of formula (4) is allowed to react with an appropriate amine at elevated temperature (100°-180° C.), preferably in the presence of an acid acceptor, such as triethylamine. One equivalent of sodium hydride may be used to enhance the nucleophilic reaction. The reaction may be carried out neat, or in an inert organic solvent.

Compounds where $R^6$ is (C$_2$-C$_4$) acyl were prepared by reacting amines of formula (1) where $R^6$ is H, with an acylating agent, such as an acetyl chloride or acetic anhydride.

Synthesis of Compounds Wherein Z is CR$^7$R$^8$

The compounds of formula (1) wherein Z is CR$^7$R$^8$ can be made using known procedures, described, for example in *J. Heterocyclic Chemistry*, Vol. 14, p. 1081–1083 (1977) by A. Scoville and F. X. Smith; and R. Cutler et al. *J. Am. Chem. Soc.* 71, (1949).

The first reference describes a process in which 5-alkyl-5-(4-quinolinyl)barbituric acids were obtained from the reaction of 4-chloroquinolines with 5-alkylbarbituric acids by heating in the absence of solvent. These products were then hydrolyzed and decarboxylated by dissolving them in a solution of sodium hydroxide in water, refluxing, then making the solution slightly acidic with hydrochloric acid, and refluxing again, to give the corresponding 4-alkylated quinolines.

The second reference describes a process in which the sodium salt of a phenyl acetonitrile is allowed to react with 4,7-dichloroquinoline in benzene at reflux. The resulting substituted nitrile is decyanated in refluxing n-butanol containing HCl.

Synthesis of Compounds Wherein Z is S

Compounds of formula (1) wherein Z is S are prepared by condensing a compound of formula (4), as previously defined, with a benzyl thiol of formula (8)

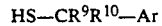

where $R^9$, $R^{10}$, and Ar are as previously defined. The reaction is typically carried out in the presence of strong base, such as sodium hydride, in a non-reactive solvent such as DMF at a temperature range of 0° to 25° C.

Synthesis of Compounds Wherein Z is SO or SO$_2$

Compounds of formula (1) wherein Z is SO or SO$_2$ are prepared by oxidizing the corresponding compounds wherein E is S using a conventional oxidation procedure, for example using m-chloroperoxybenzoic acid, hydrogen peroxide, or another conventional oxidizing agent in a non-reactive organic solvent, such as methylene chloride or chloroform, at room temperature.

Derivatives

N-oxides of the compounds of formula (1) are prepared by reacting the compound of formula (1) with an oxidizing agent, such as 3-chloroperoxybenzoic acid or hydrogen peroxide, in a non-reactive organic solvent, such as methylene chloride or chloroform, at $-20°$ C. to room temperature, preferably at about $0°$ C.

The acid addition salts of compounds of formula (1) are obtained in the usual way.

Accordingly, the invention also provides a process for preparing compounds of formula (1) which comprises a) condensing a compound of formula (4):

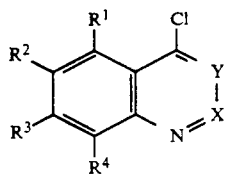   (4)

where $R^1$ to $R^4$, X, and Y are as defined in formula (1), with an alcohol of the formula (5)

   (5)

wherein $R^9$, $R^{10}$, and Ar are as defined for formula (1) in the presence of a strong base to produce a compound of formula (1) wherein Z is O, or b) reacting a compound of formula (7)

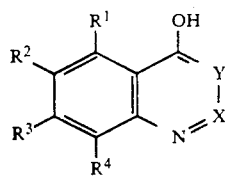   (7)

where $R^1$ to $R^4$, X, and Y are as defined for formula (1) with an alcohol of formula (5)

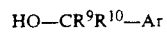   (5)

as defined above, in an aprotic solvent in the presence of at least one equivalent each of diethyl azodicarboxylate and triphenylphosphine to produce a compound of formula (1) wherein Z is O, or c) reacting a compound of formula (4), as defined above, with an amine of the formula (6)

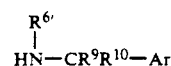   (6)

where $R^{6'}$ is M or ($C_1$-$C_4$) alkyl and $R^9$, $R^{10}$, and Ar are as defined for formula (1) to provide a compound of formula (1) wherein Z is $NR^{6'}$, or d) reacting a compound of formula (1) wherein Z is NH with an ($C_2$-$C_4$) acylating agent to produce a compound of formula (1) wherein Z is $NR^6$ where $R^6$ is ($C_2$-$C_4$) acyl, or e) reacting a compound of formula (4) as defined above, with the sodium salt of a substituted acetonitrile of the formula (9)

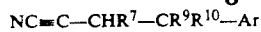   (9)

where $R^7$, $R^9$, $R^{10}$, and Ar are as previously defined, followed by acid catalyzed decyanation to produce a compound of formula (1) wherein Z is $CHR^7$; or f) reacting a compound of formula (4), as previously defined, with a benzyltthiol of formula (8)

   (8)

where $R^9$, $R^{10}$, and Ar are as defined for formula (1) in the presence of a strong base to produce a compound of formula (1) wherein Z is S, or g) oxidizing a compound of formula (1) wherein Z is S using a conventional procedure to produce a compound of formula (1) wherein Z is SO, or h) oxidizing a compound of formula (1) wherein Z is S using a conventional procedure to produce a compound of formula (1) wherein Z is $SO_2$, or i) oxidizing a compound of formula (1) wherein Y is $CR^5$ using a conventional procedure to produce the corresponding N-oxide, or j) hydrolyzing and decarboxylating a compound of the formula

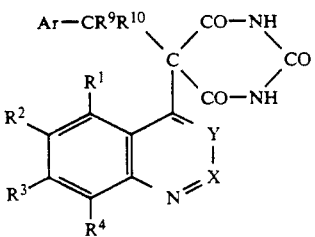   (10)

to provide a compound of formula (1) wherein Z is $CR^9R^{10}$.

Preparation of Quinoline Starting Materials

Quinoline starting materials can be synthesized using a variety of known procedures.

*Organic Syntheses*, collective volume 3, 1955, pp. 272-75, gives a procedure for preparing 4,7-dichloroquinoline, and other polysubstituted quinolines. Another general procedure is described in *Tetrahedron*, vol. 41, pp. 3033-36 (1985).

Many of the quinoline starting materials used in the following examples were prepared by the protocol shown in the following reaction scheme:

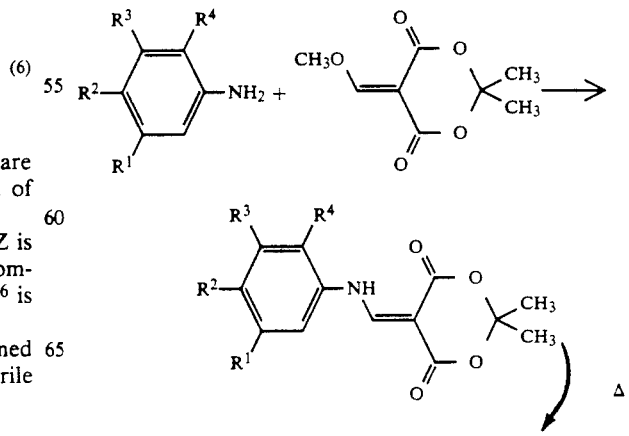

-continued

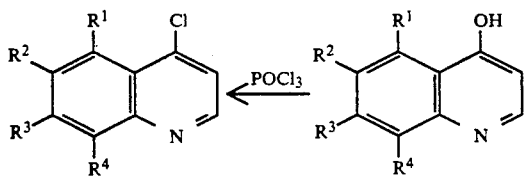

In cases where mixtures of isomeric products were obtained, the mixture of substituted 4-quinolones was chlorinated under standard conditions, and the mixture of 4-chloroquinolines was separated by liquid chromatography.

4,5-dichloroquinoline was prepared by reacting 3-chloroaniline with acrylic acid in water at ambient temperature for two days. The crude product was then isolated and heated to 100° C. in solution with an excess of polyphosphoric acid, thereby furnishing a mixture of 5- and 7-chlorodihydroquinolin-4-ones. Chromatographic separation of the 5-chloro analog, followed by treatment with iodine in hot glacial acetic acid provided 4-hydroxy-5-chloroquinoline, which was halogenated to provide the desired intermediate. (French Patent 1,514,280).

Other 4-chloro-5-substituted quinolines were prepared by converting the corresponding 5-substituted quinoline to the N-oxide, chlorinating, and separating the resulting mixture of 4-chloro and 2-chloro isomers using HPLC.

The 5-fluoro and 5-bromo quinolines can be prepared using the same general procedure. *J.A.C.S.*, vol. 71, 1785 (1949). The bromo-quinolines can then be lithiated and quenched with suitable electrophiles at low temperatures to provide other 5-substituted quinolines. *Justus Lebigs Ann. Chem.*, vol. 696, p. 98 (1966).

Preparation of nitroquinolines is disclosed in *J.A.C.S.*, vol. 68, p. 1267 (1946). Nitration of 4-chloroquinoline proceeds cleanly to deliver a mixture of 5- and 8-nitro-4-chloroquinolines, which can be separated by liquid chromatography. The 6- and 7- nitro compounds can be made via decarboxylation of the silver salts of the appropriate nitroquinoline-3-carboxylic acid.

Preparation of Quinazoline Starting Materials

Quinazoline starting materials are commercially available or readily prepared using conventional procedures. For example, 4-hydroxy quinazolines can be prepared from commercially available anthranilic acids via condensation with excess formamide at reflux (M. Endicott et al. *J. Am. Chem. Soc.*, 1946, 68, 1299). Alternatively hydroxy quinazolines can be prepared in dioxane at reflux using Gold's reagent (J. Gupton; Correia, K.; Hertel, G. *Synthetic Communications*, 1984, 14, 1013). Once in hand, the 4-hydroxy quinazoline is chlorinated under standard conditions, using for example phosphorus pentachloride in phosphorus oxychloride, to provide 4-chloroquinazoline starting materials. The 4-hydroxy quinazoline derivatives can advantageously be chlorinated using the chlorinating reagents and procedure disclosed in U.S. Pat. No. 4,230,644.

Preparation of Cinnoline Starting Materials

Cinnoline analogs are prepared via published methods. (C. M. Atkinson and J. C. Simpson—*J. Chem. Soc. London*, 1947, 232). The substituted 2-aminoacetophenone is diazotized at 0°–5° C. in water using sodium nitrite and mineral acid, and the intermediate diazonium salt is trapped by the enolic component of the ketone to provide the requisite 4-hydroxycinnoline. Routine chlorination provides the desired intermediates.

Preparation of Benzyl Alcohol Starting Materials

The benzyl alcohol starting materials of formula (8) are readily prepared using conventional chemistry.

Benzyl alcohols of formula (5) wherein $R^9$ and $R^{10}$ are different exist as enantiomers, which can be prepared separately, if desired. For example, 2-fluoroacetophenone was reacted with diisopinyl-chloroborane to provide a 95% entantiomeric excess of (S)-1-(2-fluorophenyl)ethanol. This optically active benzyl alcohol was separately reacted with sodium hydride in DMF and 4,7-dichloroquinoline to produce the (S) isomer of 7-chloro-4-(1-(2-fluorophenyl)ethoxy)-quinoline, and with diethylazodicarboxylate, triphenylphosphine and 7-chloro-4-hydroxy-quinoline to produce the (R) isomer.

EXAMPLES 1 TO 98

The following table identifies compounds actually prepared by the above described general procedures, and gives each compound's melting point. Specific illustrative preparations of the compounds of Examples 2, 13, 43, and 56 follow the table.

| EXAMPLE NUMBER | COMPOUND | M.P. |
|---|---|---|
| 1 | 4-(2-phenylethyl)quinoline | 97–99° C. |
| 2 | N-[[3-(trifluoromethyl)phenyl]methyl]-4-quinazolinamine | 145–146° C. |
| 3 | N-(phenylmethyl)-4-quinolinamine | 131–132° C. |
| 4 | 6-chloro-4-[(2,6-dichlorophenyl)methoxy]-2-methylquinoline | 191° C. |
| 5 | N-[(4-chlorophenyl)methyl]-8-fluoro-4-quinolinamine | 213–215° C. |
| 6 | 7-chloro-4-[1-(2-fluorophenyl)ethoxy]quinoline, 1-oxide | 132–134° C. |
| 7 | 7-chloro-4-(1-(2,4-dichlorophenyl)ethoxy)quinoline | 108–110° C. |
| 8 | 4-[2-[4-(*t-butyl*)phenyl]*ethyl*]-8-fluoroquinoline | 96–98° C. |
| 9 | 7-chloro-4-[[1-(2-fluorophenyl)-1-propenyl]oxy]quinoline | oil |
| 10 | 4-[1-(4-fluorophenyl)ethoxy]-7-chloroquinoline | 57–58° C. |
| 11 | N-[[4-(trifluoromethyl)phenyl]methyl]-4-quinazolinamine | 215–217° C. |
| 12 | N-[1-(4-chlorophenyl)ethyl]-8-fluoro-4-quinolinamine | 103–104° C. |
| 13 | 7-chloro-4-[1-(2-fluorophenyl)ethoxy]quinoline | 53–54° C. |
| 14 | 7-chloro-4-[1-(3-fluorophenyl)ethoxy]quinoline | 108–110° C. |
| 15 | N-[[2-(trifluoromethyl)phenyl]methyl]-4-quinazolinamine | 161–163° C. |
| 16 | 4-(1-(2-fluorophenyl)ethoxy)-5,7-dichloroquinoline | 80–81° C. |
| 17 | 8-fluoro-4-[[4-(*i-propyl*)phenyl]methoxy]quinoline | |
| 18 | 8-fluoro-N-(2-thienylmethyl)-4-quinolinamine | 163–164° C. |
| 19 | 8-fluoro-N-(2-furanylmethyl)-4-quinolinamine | 149–150° C. |
| 20 | 7-chloro-4-[(2,4-difluorophenyl)methoxy]quinoline | 96–98° C. |
| 21 | 5,7-dichloro-4-[[2-(trifluoromethyl)phenyl]methoxy]quinoline | 107–108° C. |
| 22 | 4-[1-(2,6-dichlorophenyl)ethoxy]- | 75° C. |

| EXAMPLE NUMBER | COMPOUND | M.P. |
|---|---|---|
| 23 | 4-(phenylmethoxy)quinazoline | 35° C. |
| 24 | 4-[[4-(*t-butyl*)phenyl]*methoxy*]-quinazoline | 85° C. |
| 25 | N-methyl-N-[[4-(trifluoromethyl)-phenyl]methyl]-4-quinazolinamine | 57–59° C. |
| 26 | 8-chloro-4-[(2-chlorophenyl)-methoxy]quinoline | 80–83° C. |
| 27 | 7-chloro-4-[1-(2-fluoro-phenyl)propoxy]quinoline | 61–62° C. |
| 28 | 7-chloro-4-[(2-chloro-4-fluorophenyl)methoxy]-quinoline | 120–122° C. |
| 29 | 8-chloro-4-[(2-chloro-4-fluorophenyl)methoxy]quinoline | 110–112° C. |
| 30 | 7-chloro-4-[(4-fluoro-phenyl)methoxy]quinoline | 104–106° C. |
| 31 | 7-chloro-N-[(4-chlorophenyl)-methyl]-4-quinolinamine | 160–165° C. |
| 32 | 8-chloro-N-[1-(4-fluorophenyl)-ethyl]-4-quinolinamine | 83–85° C. |
| 33 | 8-fluoro-N-[1-(4-fluorophenyl)-ethyl]-4-quinolinamine | 48–50° C. |
| 34 | (S)-7-chloro-4-(1-(2-fluoro-phenyl)ethoxy)quinoline | oil |
| 35 | (R)-7-chloro-4-(1-(2-fluoro-phenyl)ethoxy)quinoline | oil |
| 36 | 7-chloro-4-((2-fluorophenyl)-methoxy)quinoline | 108–110° C. |
| 37 | 8-fluoro-4-[1-(2,6-dichloro-phenyl)ethoxy]quinoline | 148° C. |
| 38 | 4-(cyclohexylmethoxy)quinoline | oil |
| 39 | N-4-quinazolinyl-N-[[2-(tri-fluoromethyl)phenyl]methyl]-acetamide | 109–110° C. |
| 40 | N-4-quinazolinyl-N-[[4-(tri-fluoromethyl)phenyl]methyl]-acetamide | 84–86° C. |
| 41 | 8-fluoro-4-(phenylmethoxy)-quinoline | 97–98° C. |
| 42 | 4-[(4-chlorophenyl)methoxy]-8-fluoroquinoline | 125–126° C. |
| 43 | 4-[1-[4-(*t-butyl*)phenyl]*ethoxy*]-quinazoline | 85–86° C. |
| 44 | 4-[[4-(*t-butyl*)phenyl]*methoxy*]-8-fluoroquinoline | 104–105° C. |
| 45 | 4-[1-[4-(*t-butyl*)phenyl]*ethoxy*]-8-fluoroquinoline | 114–115° C. |
| 46 | 8-fluoro-4-[1-(4-methylphenyl)-ethoxy]quinoline | 67–68° C. |
| 47 | 4-[(4-chlorophenyl)methoxy]-quinazoline | 102–103° C. |
| 48 | 8-fluoro-4-[(4-fluorophenyl)-methoxy]quinoline | 145–146° C. |
| 49 | 4-(cyclohexylmethoxy)-8-fluoro-quinoline | 93–95° C. |
| 50 | 4-[1-(2,5-dimethylphenyl)ethoxy]-quinazoline | 65° C. |
| 51 | 8-fluoro-4-[1-(3,4-dichlorophenyl)-ethoxy]quinoline | 85° C. |
| 52 | 4-[1-[2,6-dimethyl-4-(*t-butyl*)-phenyl]ethoxy]quinoline | 140° C. |
| 53 | 4-[1-[4-(*t-butyl*)-2,6-*dimethyl*-phenyl]ethoxy]-8-fluoroquinoline | 165° C. |
| 54 | 7-chloro-[[4-(*t-propyl*)phenyl]-methoxy]quinoline | 196–198° C. |
| 55 | 7-chloro-4-((2-(trifluoro-methyl)phenyl)methoxy)quinoline | 111–112° C. |
| 56 | 8-fluoro-4-[2-(3-thienyl)ethyl]-quinoline | 96–97° C. |
| 57 | 4-furfurylaminoquinazoline | |
| 58 | N-(2,2-diphenylpropyl)-4-quinolin-amine | 110–111° C. |
| 59 | 4-[bis(4-fluorophenyl)methoxy]-7-chloroquinoline | 195–200° C. |
| 60 | N-[[4-(*t-butyl*)phenyl]*methyl*]-4-quinazolinamine | 155–157° C. |
| 61 | N-(2,2-diphenylpropyl)-8-fluoro-4-quinolinamine | 56–58° C. |
| 62 | 7-chloro-4-[(2-chlorophenyl)-methoxy]quinoline | 100–101° C. |
| 63 | 8-fluoro-4-[1-(2,5-dimethylphenyl)-ethoxy]quinoline | 148° C. |
| 64 | 4-[[3-(trifluoromethyl)phenyl]-methylthio]quinazoline | 60–62° C. |
| 65 | 4-[[3-(trifluoromethyl)phenyl]-methylsulfonyl]quinazoline | 97–99° C. |
| 66 | 4-[(1,1'-bisphenyl)-4-ylmethyl-thio]quinazoline | 148–150° C. |
| 67 | 8-fluoro-4-[[4-(*t-butyl*)phenyl]-methylsulfonyl]quinazoline | 85–87° C. |
| 68 | 4-[[4-(*t-butyl*)phenyl]*methylthio*]-quinazoline | 90–92° C. |
| 69 | N-(1-naphthalenylmethyl)-4-quinazo-linamine | 190–192° C. |
| 70 | S-(+)-7-chloro-N-(1-phenylethyl)-4-quinazolinamine | 143–145° C. |
| 71 | R-(−)-7-chloro-N-(1-phenylethyl)-4-quinazolinamine | 144–145° C. |
| 72 | 8-fluoro-4-[1-(2-naphthalenyl)-ethoxy]quinazoline | oil |
| 73 | N-[[4-(trifluoromethoxy)phenyl]-methyl]-4-quinazolinamine | 177–179° C. |
| 74 | N-[[4-(trifluoromethoxy)phenyl]-methyl]-N-4-quinazolinylacetamide | 78–80° C. |
| 75 | 7-chloro-4-(cyclopentylmethoxy)-quinoline | 85–87° C. |
| 76 | 7-chloro-4-[(1-methylcyclopentyl)-methoxy]quinoline | 67–68° C. |
| 77 | (+)-7-chloro-4-(1-phenylethoxy)-quinoline | oil |
| 78 | (−)-7-chloro-4-(1-phenylethoxy)-quinoline | N/A |
| 79 | 7-trifluoromethyl-4-[[4-(*t-butyl*)-phenyl]methylthio]quinoline | 78–80° C. |
| 80 | 4-[1-(1-naphthalenyl)ethoxy]-quinazoline | 97–99° C. |
| 81 | 7-trifluoromethyl-4-[[4-(*t-butyl*)-phenyl]methylsulfonyl]quinoline | 138–140° C. |
| 82 | 8-fluoro-4-[[3-(trifluoromethyl)-phenyl]methylthio]quinoline | 103–105° C. |
| 83 | 8-fluoro-4-[[4-(*t-butyl*)phenyl]-methylthio]quinoline | 135–137° C. |
| 84 | 4-(cyclohexylmethoxy)quinazoline | N/A |
| 85 | 4-(cyclohexylmethoxy)-8-fluoro-quinoline | N/A |
| 86 | 1-[3-[[(6-fluoro-2-methyl-4-quinolinyl)oxy]methyl]-4-methoxy-phenyl]ethanone | 195° |
| 87 | 7-chloro-4-[2-(2-fluorophenyl)-vinyl]quinoline | 60–61° C. |
| 88 | 4-[bis-(2-fluorophenyl)methoxy]-7-chloroquinoline | 238–240° C. |
| 89 | 8-chloro-4-[(2-bromophenyl)methoxy]-quinoline | 133–135° C. |
| 90 | 8-chloro-4-(2-furanylmethoxy)-quinoline | 108–110° C. |
| 91 | 7-chloro-4-(2-furanylmethoxy)-quinoline | 91–92° C. |
| 92 | 7-chloro-4-[(4-tetraethoxyphenyl)-methoxy]quinoline | 113–114° C. |
| 93 | 8-chloro-4-[[4-(1,1,2,2-tetra-fluoroethoxy)phenyl]methoxy]quino-line | 115–117° C. |
| 94 | 8-chloro-4-[(1-methylcyclopentyl)-methoxy]quinoline | 80–81° C. |
| 95 | 7-chloro-4-[(2-chloro-5-thienyl)-methoxy]quinoline | 130–132° C. |
| 96 | 8-chloro-4-[(2-chloro-5-thienyl)-methoxy]quinoline | 143–145° C. |
| 97 | 7-chloro-4-[(2,3-dihydro-1,4-benzo-dioxin-2-yl)methoxy]quinoline | 115–117° C. |
| 98 | 4-[(2-chloro-5-pyridinyl)methoxy]-quinazoline | 137–139° C. |

The following detailed descriptions of the procedures used to prepare selected Examples are representative of the procedures used to prepare the compounds of the other Examples.

EXAMPLE 2

N-[[3-(Trifluoromethyl)phenyl]methyl]-4-quinazolinamine

A mixture of 1.65 g of 4-chloroquinazoline, 1.5 g of [3-(trifluoromethyl)phenyl]methyl amine, and 1.0 g of triethylamine in 50 ml of ethanol was refluxed for 6 hours. The mixture was then cooled, and washed with water. After removing solvents in vacuo the product was crystallized from a mixture of ethyl acetate and hexane. Yield: 1.0 g. M.P. 145°–146° C.

EXAMPLE 13

7-Chloro-4-[1-(2-fluorophenyl)ethoxy]quinoline

A solution of 2.52 g (18 mmol) of 1-(2-fluorophenyl)ethanol in DMF was added dropwise to a mixture of 2.97 g (15mmol) of 4,7-dichloroquinoline and 0.50 g (21 mmol) of sodium hydride in 15 ml of DMF. After addition was complete, the mixture was heated to 160° C. After four hours the mixture was allowed to cool and 0.1 g of sodium hydride was added. Upon completion of the reaction, a few drops of water were carefully added to destroy excess sodium hydride. Then the solution was poured into water. The product was extracted into ethyl acetate, the ethyl acetate solution was washed three times with water, then dried, and evaporated, producing an oil that crystallized from heptane/ethyl acetate. Yield: 0.77 g M.P. 53°–54° C.

EXAMPLE 43

4-[1-[4-(t-Butyl)phenyl]ethoxy]quinazoline

To a mixture of 0.5 g of sodium hydride in 100 ml of DMF was added 2.0 g of 1-[4-(t-butyl)phenyl]ethanol, and the resulting mixture was stirred at room temperature for one hour. Then 1.8 g of 4-chloroquinazoline in 30 ml of DMF were added. The mixture was stirred at room temperature for three hours, then poured into an ice/water mixture. The product was extracted into ether, the ether solution was concentrated and the residue was recrystallized from a pentane/ethyl acetate mixture to give 0.300 g of the title product. M.P. 85°–86° C.

EXAMPLE 56

8-Fluoro-4-[2-(3-thienyl)ethyl]quinoline

A mixture of 1.85 g of 5-[2-(3-thienyl)ethyl]-barbituric acid and 1.5 g of 4-chloro-8-fluoroquinoline was heated to 150° C. for 1¼ hours, then cooled. To the cooled mixture were added 2 g of NaOH and 35 ml of water, and the mixture was heated to reflux overnight. The mixture was cooled, then acidified to pH 1.5 with concentrated HCl, and heated gently for about 1¼ hours. After cooling the mixture, the product was extracted into $CH_2Cl_2$. The $CH_2Cl_2$ solution was filtered through phase separating paper, then evaporated in vacuo, giving about 2 g of oil residue. The residue was absorbed onto silica gel and chromatographed, eluting with $CH_2Cl_2$. Fractions containing product were combined, and the title product was crystallized. Recrystallization from petroleum ether/ $CH_2Cl_2$ gave 0.68 g of the title product. M.P. 96°–97° C.

Utility

The compounds of the present invention have been found to control fungi, particularly plant pathogens. When employed in the treatment of plant fungal diseases, the compounds are applied to the plants in a "disease inhibiting and phytologically acceptable amount." The term "disease inhibiting and phytologically acceptable amount" as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 4 lb/A. The compounds of the invention may also be used to protect stored grain and other non-plant loci from fungal infestation.

Greenhouse Tests

The following experiments were performed in the laboratory to determine the fungicidal efficacy of the compounds of the invention.

Plant Pathology Screen

This screen was used to evaluate the efficacy of the present compounds against a variety of different organisms that cause plant diseases.

The test compounds were formulated for application by dissolving 50 mg of the compound into 1.25 ml of solvent. The solvent was prepared by mixing 50 ml of "Tween 20" (polyethylene (20) sorbitan monolaurate emulsifier) with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Following Tables | Host |
| --- | --- | --- |
| Erysiphe graminis tritici (powdery mildew) | POWD MDEW | wheat |
| Pyricularia oryzae (rice blast) | RICE BLAS | rice |
| Puccinia recondita tritici (leaf rust) | LEAF RUST | wheat |
| Botrytis cinerea (gray mold) | GRAY MOLD | grape berries |
| Pseudoperonospora cubensis (downy mildew) | DOWN MDEW | squash |
| Cercospora beticola (leaf spot) | LEAF SPOT | sugar beet |
| Venturia inaequalis (apple scab) | APPL SCAB | apple seedling |
| Septoria tritici (leaf blotch) | LEAF BLOT | wheat |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2–4 hours.

The effectiveness of test compounds in controlling disease was rated on the following scale.

0 = not tested against specific organism
− = 0–19% control at 400 ppm
+ = 20–89% control at 400 ppm
++ = 90–100% control at 400 ppm
+++ = 90–100% control at 100 ppm Table 1 presents the activity of typical compounds of the present invention when evaluated in this experiment:

TABLE 1

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 1 | ++ | − | − | − | − | − | − | + |
| 2 | ++ | ++ | +++ | − | +++ | + | − | +++ |
| 3 | + | + | − | − | ++ | 0 | 0 | 0 |
| 4 | − | − | − | − | − | 0 | 0 | 0 |
| 5 | − | + | + | − | ++ | ++ | − | + |
| 6 | +++ | +++ | ++ | − | + | 0 | 0 | 0 |
| 7 | ++ | − | − | − | − | 0 | 0 | 0 |
| 8 | + | + | + | − | − | 0 | 0 | 0 |
| 9 | ++ | + | + | − | ++ | 0 | 0 | 0 |
| 10 | +++ | ++ | + | − | + | − | − | − |
| 11 | + | + | − | − | + | 0 | 0 | 0 |
| 12 | + | ++ | ++ | − | ++ | ++ | + | + |
| 13 | +++ | ++ | + | − | +++ | − | − | − |
| 14 | +++ | − | − | − | − | − | − | − |
| 15 | +++ | + | ++ | − | +++ | ++ | − | + |
| 16 | + | − | − | − | ++ | + | − | + |
| 17 | − | + | + | − | + | 0 | 0 | 0 |
| 18 | + | + | ++ | − | ++ | + | − | − |
| 19 | − | + | + | − | + | − | − | − |
| 20 | ++ | + | + | − | − | 0 | 0 | 0 |
| 21 | + | + | − | − | − | − | − | − |
| 22 | ++ | ++ | ++ | − | +++ | 0 | 0 | 0 |
| 23 | + | + | ++ | − | + | 0 | 0 | 0 |
| 24 | − | + | − | − | − | 0 | 0 | 0 |
| 25 | ++ | ++ | ++ | − | ++ | 0 | 0 | 0 |
| 26 | − | − | − | − | + | 0 | 0 | 0 |
| 27 | +++ | ++ | + | − | ++ | 0 | 0 | 0 |
| 28 | + | − | − | − | − | 0 | 0 | 0 |
| 29 | − | − | − | − | − | 0 | 0 | 0 |
| 30 | ++ | − | − | − | − | − | − | ++ |
| 31 | ++ | + | − | − | ++ | + | − | − |
| 32 | − | + | + | − | ++ | + | − | − |
| 33 | + | + | ++ | − | ++ | + | + | − |
| 34 | ++ | ++ | + | − | + | 0 | 0 | 0 |
| 35 | +++ | ++ | + | − | ++ | 0 | 0 | 0 |
| 36 | ++ | + | − | − | − | 0 | 0 | 0 |
| 37 | − | + | − | − | ++ | 0 | 0 | 0 |
| 38 | + | − | − | − | − | 0 | 0 | 0 |
| 39 | ++ | − | − | − | − | − | − | − |
| 40 | + | + | − | − | + | − | − | − |
| 41 | + | + | ++ | − | ++ | − | +++ | +++ |
| 42 | − | + | − | − | − | 0 | 0 | 0 |
| 43 | ++ | + | + | − | + | − | − | + |
| 44 | − | − | − | − | − | 0 | 0 | 0 |
| 45 | − | + | + | − | + | + | − | + |
| 46 | + | + | + | − | + | + | + | + |
| 47 | + | − | − | − | − | 0 | 0 | 0 |
| 48 | − | − | − | − | − | 0 | 0 | 0 |
| 49 | + | + | + | − | ++ | 0 | 0 | 0 |
| 50 | + | ++ | + | − | ++ | 0 | 0 | 0 |
| 51 | + | ++ | + | − | + | 0 | 0 | 0 |
| 52 | + | − | − | − | − | 0 | 0 | 0 |
| 53 | − | − | − | − | − | 0 | 0 | 0 |
| 54 | − | − | − | − | − | 0 | 0 | 0 |
| 55 | +++ | + | − | − | + | + | − | +++ |
| 56 | − | +++ | +++ | − | + | − | +++ | − |
| 57 | − | + | + | − | ++ | + | − | − |
| 58 | + | + | ++ | − | ++ | + | − | − |
| 59 | + | − | + | − | − | 0 | 0 | 0 |
| 60 | + | +++ | +++ | − | +++ | 0 | 0 | 0 |
| 61 | + | ++ | ++ | − | +++ | + | − | − |
| 62 | + | − | − | − | − | 0 | 0 | 0 |
| 63 | − | − | − | 0 | ++ | 0 | 0 | 0 |
| 64 | + | + | − | − | − | 0 | 0 | 0 |
| 65 | − | + | − | − | − | 0 | 0 | 0 |
| 66 | − | − | − | − | + | 0 | 0 | 0 |
| 67 | − | + | + | − | − | 0 | 0 | 0 |
| 68 | − | − | − | − | − | 0 | 0 | 0 |
| 69 | − | + | ++ | − | + | 0 | 0 | 0 |
| 70 | + | ++ | ++ | − | ++ | 0 | 0 | 0 |
| 71 | − | + | + | − | +++ | − | − | − |

TABLE 1-continued

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 72 | ++ | ++ | ++ | − | ++ | 0 | 0 | 0 |
| 73 | +++ | +++ | +++ | − | +++ | 0 | 0 | 0 |
| 74 | + | ++ | + | − | ++ | 0 | 0 | 0 |
| 75 | +++ | + | + | − | − | 0 | 0 | 0 |
| 76 | ++ | ++ | + | − | + | 0 | 0 | 0 |
| 77 | +++ | ++ | ++ | + | + | 0 | 0 | 0 |
| 78 | +++ | + | + | − | + | 0 | 0 | 0 |
| 79 | − | − | − | − | − | 0 | 0 | 0 |
| 80 | + | − | − | − | − | 0 | 0 | 0 |
| 81 | − | + | − | − | ++ | 0 | 0 | 0 |
| 82 | + | − | − | − | − | 0 | 0 | 0 |
| 83 | − | − | − | − | − | 0 | 0 | 0 |
| 84 | + | − | − | − | − | 0 | 0 | 0 |
| 85 | + | + | + | − | ++ | 0 | 0 | 0 |
| 86 | − | − | − | − | − | 0 | 0 | 0 |
| 87 | + | ++ | − | − | − | 0 | 0 | 0 |
| 88 | − | − | − | − | − | 0 | 0 | 0 |
| 89 | − | − | − | − | + | 0 | 0 | 0 |
| 90 | − | + | − | − | − | 0 | 0 | 0 |
| 91 | + | + | + | − | + | 0 | 0 | 0 |
| 92 | ++ | − | − | − | − | 0 | 0 | 0 |
| 93 | − | − | − | − | − | 0 | 0 | 0 |
| 94 | + | + | + | − | ++ | 0 | 0 | 0 |
| 95 | + | − | − | − | − | 0 | 0 | 0 |
| 96 | − | + | − | − | − | 0 | 0 | 0 |
| 97 | + | + | − | − | 0 | 0 | 0 | 0 |
| 98 | − | − | ++ | − | + | 0 | 0 | 0 |

Representative compounds were further tested in the greenhouse against various pathogens. The compounds were formulated and applied as foliar sprays as in Test 1. Results are reported in the following Tables, wherein the rating scale of Table 1 is used.

The following abbreviations are used:
PM = Wheat Powdery Mildew
RB = Rice Blast
TLB = Tomato Late Blight
GDM = Grape Downy Mildew
AS = Apple Scab
LB = Wheat Leaf Blot
LR = Wheat Leaf Rust
RR = Rice Rhizoctonia Sheath Blight
APM = Apple Powdery Mildew

TABLE 2

| COMPOUND EXAMPLE NUMBER | PM | RB | TLB | GDM | AS |
|---|---|---|---|---|---|
| 2 | 0 | + | +++ | +++ | 0 |
| 5 | 0 | 0 | +++ | ++ | 0 |
| 6 | 0 | − | 0 | 0 | 0 |
| 10 | +++ | 0 | 0 | 0 | 0 |
| 12 | 0 | 0 | +++ | +++ | 0 |
| 13 | +++ | + | + | ++ | 0 |
| 14 | +++ | 0 | 0 | 0 | 0 |
| 15 | +++ | 0 | − | ++ | + |
| 16 | + | 0 | 0 | 0 | 0 |
| 27 | +++ | 0 | 0 | 0 | 0 |
| 30 | + | 0 | 0 | 0 | 0 |
| 34 | +++ | 0 | 0 | 0 | 0 |
| 35 | +++ | 0 | 0 | 0 | 0 |
| 58 | 0 | 0 | + | + | 0 |
| 61 | 0 | 0 | ++ | ++ | 0 |
| 73 | 0 | 0 | 0 | ++ | 0 |
| 75 | ++ | 0 | 0 | 0 | 0 |
| 78 | +++ | 0 | 0 | 0 | 0 |

TABLE 3

| COMPOUND EXAMPLE NUMBER | LB | LR | RR | APM |
|---|---|---|---|---|
| 2 | 0 | ++ | 0 | 0 |
| 5 | 0 | 0 | 0 | 0 |
| 10 | 0 | 0 | 0 | 0 |
| 12 | 0 | 0 | 0 | 0 |
| 13 | + | 0 | + | ++ |
| 14 | 0 | 0 | 0 | 0 |
| 15 | 0 | + | 0 | 0 |
| 16 | 0 | 0 | 0 | 0 |
| 30 | 0 | 0 | 0 | 0 |
| 34 | 0 | 0 | 0 | 0 |
| 35 | 0 | 0 | 0 | 0 |
| 58 | 0 | 0 | 0 | 0 |
| 61 | 0 | 0 | 0 | 0 |

Field Tests 7-chloro-4-[1-(2-fluorophenyl)ethoxy]ethoxy]quinoline was field tested against a variety of plant pathogens. The following table reports pathogens against which it showed activity in these tests.

| COMPOUND EX. NO. | CROP | PATHOGEN |
|---|---|---|
| 13 | barley | Rhynchosporium secalis |
| | | Pyrenophora teres |
| | | Erysiphe graminis hordei |
| | cucumber | Sphaerotheca fuliginea |
| | wheat | Pseudocercosporella herpotrichoides |
| | | Erysiphe graminis hordei |

Fungal disease pathogens are known to develop resistance to fungicides. When strains resistant to a fungicide develop, it becomes necessary to apply larger and larger amounts of the fungicide to obtain desired disease control. To retard the development of resistance to new fungicides, it is desirable to apply the new fungicides in combination with other fungicides. Use of a combination product also permits the product's spectrum of activity to be adjusted.

Accordingly, another aspect of the invention is a fungicidal combination comprising at least 1% by weight of a compound of formula (1) in combination with a second fungicide.

Contemplated classes of fungicides from which the second fungicide may be selected include:

1) N-substituted azoles, for example propiconazole, triademefon, flusilazol, diniconazole, ethyltrianol, myclobutanil, and prochloraz;

2) pyrimidines, such as fenarimol and nuarimol;

3) morpholines, such as fenpropimorph and tridemorph;

4) piperazines, such as triforine; and 5) pyridines, such as pyrifenox. Fungicides in these five classes all function by inhibiting sterol biosynthesis. Additional classes of contemplated fungicides, which have other mechanisms of action, include:

6) dithiocarbamates, such as maneb and mancozeb;

7) phthalimides, such as captafol;

8) isophthalonitrites, such as chlorothalonil;

9) dicarboximides, such as iprodione;

10) benzimidazoles, such as benomyl and carbendazim;

11) 2-aminopyrimidines, such as ethirimol;

12) carboxamides, such as carboxin; and 13) dinitrophenols, such as dinocap.

The fungicide combinations of the invention contain at least 1%, ordinarily 20 to 80%, and more typically 50 to 75% by weight of a compound of formula (1).

MITE/INSECT SCREEN

The compounds of Examples 1-98 were tested for miticidal and insecticidal activity in the following mite/insect screen.

Each test compound was formulated by dissolving the compound in acetone/alcohol (50:50) mixture containing 23 g of "Toximul R" (sulfonate/nonionic blend emulsifier) and 13 g of "Toximul S" (sulfonate/nonionic blend emulsifier) per liter. These mixtures were then diluted with water to give the indicated concentrations.

Twospotted spider mites (*Tetranychus urticae* Koch) and melon aphids (*Aphis gossypii* Glover) were introduced on squash cotyledons and allowed to establish on both leaf surfaces. Other plants in the same treatment pot were left uninfested. The leaves were then sprayed with 5 ml of test solution using a DeVilbiss atomizing sprayer at 10 psi. Both surfaces of the leaves were covered until runoff, and then allowed to dry for one hour. Two uninfested leaves were then excised and placed into a Petri dish containing southern armyworm (*Spodopetra eridania* Cramer).

Activity on Southern corn rootworm (*Diabrotica undecimpuctata howardi* Barber) was evaluated by adding two ml of tap water, a presoaked corn seed, and 15 g of dry sandy soil to a one ounce plastic container. The soil was treated with 1 mL of test solution containing a predetermined concentration of test compound. After six to 12 hours of drying, five 2-3 instar corn rootworm larvae were added to the individual cups, which were then capped and held at 23° C.

After standard exposure periods, percent mortality was evaluated. Results are reported in Table 4. The following abbreviations are used in Table 4:

CRW refers to corn rootworm
SAW refers to Southern armyworm
SM refers to twospotted spider mites
MA refers to melon aphids.

TABLE 4

MITE/INSECT SCREEN

| COMPOUND | CRW RATE PPM | CRW RESULTS % | SAW SM & MA RATE PPM | SAW RESULTS % | SM RESULTS % | MA RESULTS % |
|---|---|---|---|---|---|---|
| 1 | 24.00 | 0 | 400 | 0 | 0 | 0 |
| 2 | 24.00 | 0 | 400 | 0 | 0 | 0 |
|   | 12.00 | 0 | 200 | 0 | 0 | 0 |
| 3 | 12.00 | 0 | 200 | 0 | 0 | 0 |
| 4 | 12.00 | 0 | 200 | 0 | 0 | 0 |
| 5 | 12.00 | 0 | 200 | 0 | 0 | 0 |
|   | 24.00 | 0 | 400 | 0 | 0 | 0 |
| 6 | 24.00 | 0 | 400 | 0 | 0 | 0 |
| 7 | 24.00 | 0 | 400 | 0 | 0 | 0 |
| 8 | 24.00 | 0 | 400 | 0 | 80 | 0 |
| 9 | 24.00 | 0 | 400 | 0 | 0 | 0 |
| 10 | 24.00 | 0 | 400 | 0 | 0 | 0 |
| 11 | 24.00 | 0 | 400 | 0 | 0 | 0 |
|   | 12.00 | 0 | 200 | 0 | 0 | 0 |
| 12 | 24.00 | 0 | 400 | 0 | 0 | 0 |
|   | 12.00 | 0 | 200 | 0 | 0 | 0 |
| 13 | 24.00 | 0 | 400 | 0 | 50 | 0 |
| 14 | 24.00 | 0 | 400 | 0 | 0 | 0 |
| 15 | 12.00 | 0 | 200 | 0 | 0 | 0 |
|   | 24.00 | 0 | 400 | 0 | 0 | 0 |
| 16 | 24.00 | 0 | 400 | 0 | 0 | 0 |
| 17 | 12.00 | 0 | 200 | 0 | 0 | 0 |
|   | 24.00 | 0 | 400 | 0 | 0 | 0 |
| 18 | 12.00 | 0 | 200 | 0 | 0 | 0 |
| 19 | 12.00 | 0 | 200 | 0 | 0 | 0 |
| 20 | 24.00 | 0 | 400 | 0 | 100 | 0 |
|   | 12.00 | 0 | 200 | 0 | 0 | 0 |
| 21 | 24.00 | 0 | 400 | 0 | 0 | 0 |
| 22 | 24.00 | 0 | 400 | 0 | 0 | 0 |
| 23 | 24.00 | 0 | 400 | 0 | 0 | 0 |
| 24 | 24.00 | 0 | 400 | 0 | 0 | 0 |
| 25 | 24.00 | 0 | 400 | 0 | 90 | 90 |

TABLE 4-continued

MITE/INSECT SCREEN

| COMPOUND | CRW RATE PPM | CRW RESULTS % | SAW SM & MA RATE PPM | SAW RESULTS % | SM RESULTS % | MA RESULTS % |
|---|---|---|---|---|---|---|
| | 12.00 | 0 | 200 | 80 | 50 | 0 |
| 26 | 24.00 | 0 | 400 | 0 | 0 | 0 |
| | 12.00 | 0 | 200 | 60 | 0 | 0 |
| 27 | 24.00 | 0 | 400 | 0 | 0 | 0 |
| 28 | 24.00 | 0 | 400 | 100 | 0 | 0 |
| 29 | 24.00 | 0 | 400 | 0 | 0 | 0 |
| 30 | 12.00 | 0 | 200 | 0 | 0 | 0 |
| 31 | 12.00 | 0 | 200 | 0 | 0 | 0 |
| | 24.00 | 0 | 400 | 0 | 0 | 0 |
| 32 | 12.00 | 0 | 200 | 0 | 0 | 0 |
| | 24.00 | 0 | 400 | 0 | 0 | 0 |
| 33 | 24.00 | 0 | 400 | 0 | 0 | 0 |
| | 12.00 | 0 | 200 | 0 | 0 | 0 |
| 34 | 24.00 | 0 | 400 | 0 | 0 | 0 |
| 35 | 24.00 | 0 | 400 | 0 | 0 | 0 |
| 36 | 24.00 | 0 | 400 | 0 | 0 | 0 |
| 37 | 24.00 | 0 | 400 | 0 | 0 | 0 |
| 38 | 24.00 | 0 | 400 | 0 | 0 | 0 |
| | 12.00 | 0 | 200 | 0 | 0 | 0 |
| 39 | 24.00 | 0 | 400 | 0 | 0 | 0 |
| | 12.00 | 0 | 200 | 0 | 0 | 0 |
| 40 | 24.00 | 0 | 400 | 0 | 0 | 0 |
| | 12.00 | 0 | 200 | 0 | 0 | 0 |
| 41 | 12.00 | 0 | 200 | 0 | 0 | 0 |
| | 24.00 | 0 | 400 | 0 | 0 | 0 |
| 42 | 12.00 | 0 | 200 | 0 | 0 | 0 |
| | 24.00 | 0 | 400 | 0 | 0 | 0 |
| 43 | 12.00 | 0 | 200 | 0 | 100 | 40 |
| | 24.00 | 0 | 400 | 0 | 100 | 20 |
| 44 | 12.00 | 0 | 200 | 0 | 0 | 0 |
| | 24.00 | 0 | 400 | 0 | 0 | 0 |
| 45 | 12.00 | 0 | 200 | 0 | 0 | 0 |
| | 24.00 | 0 | 400 | 0 | 0 | 0 |
| 46 | 12.00 | 0 | 200 | 0 | 0 | 0 |
| | 24.00 | 0 | 400 | 0 | 0 | 0 |
| 47 | 24.00 | 0 | 400 | 0 | 0 | 0 |
| | 12.00 | 0 | 200 | 40 | 0 | 0 |
| 48 | 12.00 | 0 | 200 | 0 | 0 | 0 |
| 49 | 12.00 | 0 | 200 | 0 | 0 | 0 |
| | 24.00 | 0 | 400 | 0 | 0 | 0 |
| 50 | 24.00 | 0 | 400 | 0 | 0 | 0 |
| 51 | 24.00 | 0 | 400 | 0 | 0 | 0 |
| 52 | 24.00 | 0 | 400 | 0 | 0 | 0 |
| 53 | 24.00 | 0 | 400 | 0 | 0 | 0 |
| 54 | 12.00 | 0 | 200 | 0 | 0 | 0 |
| | 24.00 | 0 | 400 | 0 | 0 | 0 |
| 55 | 24.00 | 0 | 400 | 0 | 0 | 0 |
| 56 | 24.00 | 0 | 400 | 0 | 0 | 0 |
| 57 | 24.00 | 0 | 400 | 0 | 0 | 0 |
| 58 | 12.00 | 0 | 200 | 0 | 0 | 0 |
| 59 | 24.00 | 0 | 400 | 0 | 0 | 0 |
| 60 | 24.00 | 0 | 400 | 0 | 0 | 0 |
| | 12.00 | 0 | 200 | 80 | 0 | 0 |
| 61 | 12.00 | 0 | 200 | 0 | 0 | 0 |
| 62 | 24.00 | 0 | 400 | 0 | 0 | 0 |
| 63 | 24.00 | 0 | 400 | 0 | 0 | 0 |
| 64 | 24.00 | 0 | 400 | 0 | 0 | 0 |
| | 12.00 | 0 | 200 | 100 | 80 | 100 |
| 65 | 24.00 | 0 | 400 | 0 | 0 | 0 |
| | 12.00 | 0 | 200 | 0 | 0 | 80 |
| 66 | 24.00 | 0 | 400 | 0 | 0 | 0 |
| | 12.00 | 0 | 200 | 0 | 0 | 0 |
| 67 | 24.00 | 0 | 400 | 0 | 0 | 0 |
| 68 | 24.00 | 0 | 400 | 0 | 0 | 0 |
| 69 | 24.00 | 0 | 400 | 0 | 0 | 0 |
| 70 | 24.00 | 0 | 400 | 0 | 0 | 0 |
| 71 | 24.00 | 0 | 400 | 0 | 0 | 0 |
| 72 | 24.00 | 0 | 400 | 0 | 40 | 80 |
| | 12.00 | 0 | 200 | 0 | 0 | 0 |
| 73 | 24.00 | 0 | 400 | 100 | 0 | 0 |
| | 12.00 | 0 | 200 | 0 | 0 | 0 |
| 74 | 24.00 | 0 | 400 | 0 | 0 | 0 |
| | 12.00 | 0 | 200 | 0 | 0 | 0 |
| 75 | 24.00 | 0 | 400 | 0 | 0 | 0 |
| 76 | 24.00 | 0 | 400 | 0 | 0 | 80 |
| | 12.00 | 0 | 200 | 0 | 0 | 0 |
| 77 | 24.00 | 0 | 400 | 0 | 0 | 0 |

TABLE 4-continued

MITE/INSECT SCREEN

| COMPOUND | CRW RATE PPM | CRW RESULTS % | SAW SM & MA RATE PPM | SAW RESULTS % | SM RESULTS % | MA RESULTS % |
|---|---|---|---|---|---|---|
| 78 | 24.00 | 0 | 400 | 0 | 0 | 0 |
| 79 | 24.00 | 0 | 400 | 0 | 0 | 0 |
|  | 12.00 | 0 | 200 | 0 | 0 | 40 |
| 80 | 24.00 | 0 | 400 | 0 | 0 | 0 |
|  | 12.00 | 0 | 200 | 0 | 80 | 100 |
| 81 | 24.00 | 0 | 400 | 0 | 0 | 0 |
|  | 12.00 | 0 | 200 | 100 | 0 | 0 |
| 82 | 24.00 | 0 | 400 | 0 | 0 | 0 |
|  | 12.00 | 0 | 200 | 0 | 0 | 0 |
| 83 | 24.00 | 0 | 400 | 0 | 0 | 80 |
|  | 12.00 | 0 | 200 | 0 | 0 | 0 |
| 84 | 24.00 | 0 | 400 | 0 | 0 | 0 |
|  | 12.00 | 0 | 200 | 0 | 0 | 0 |
| 85 | 24.00 | 0 | 400 | 0 | 0 | 0 |
|  | 12.00 | 0 | 200 | 0 | 0 | 0 |
| 86 | 12.00 | 0 | 200 | 0 | 0 | 0 |
| 87 | 24.00 | 0 | 400 | 0 | 0 | 0 |
| 88 | 24.00 | 0 | 400 | 0 | 0 | 0 |
| 89 | 24.00 | 0 | 400 | 0 | 0 | 0 |
| 90 | 24.00 | 0 | 400 | 0 | 0 | 0 |
| 91 | 24.00 | 0 | 400 | 0 | 0 | 0 |
| 92 | 24.00 | 0 | 400 | 0 | 0 | 0 |
| 93 | 24.00 | 0 | 400 | 0 | 0 | 0 |
| 94 | 24.00 | 0 | 400 | 0 | 0 | 0 |
| 95 | 24.00 | 0 | 400 | 60 | 0 | 80 |
|  | 12.00 | 0 | 200 | 100 | 0 | 0 |
| 96 | 24.00 | 0 | 400 | 0 | 0 | 0 |
| 97 | 24.00 | 0 | 400 | 0 | 0 | 0 |
| 98 | 24.00 | 0 | 400 | 0 | 0 | 0 |
|  | 12.00 | 0 | 200 | 0 | 0 | 0 |

The compounds of the invention can be used in combination with other insecticides or miticides such as, for example, carbamates, phosphates, and pyrethroids, to provide a broader spectrum of activity, or to combat or delay resistance.

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 10% to about 50% by weight of liquid, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those mentioned above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, group volcanic rock and the like. Dusts can suitably contain from about 1% to about 10% of the compound.

The following formulations of compounds of the invention are typical of compositions useful in the practice of the present invention.

| A. Emulsifiable Concentrate | |
|---|---|
| 7-Chloro-4-[1-(2-fluorophenyl)ethoxy]quinoline | 12.5% |
| "EXXON 200" (naphthalenic solvent) | 83.5% |
| "TOXIMUL D" (nonionic/anionic surfactant blend) | 3.0% |
| "TOXIMUL H" (nonionic/anionic surfactant blend) | 1.0% |

| B. Aqueous Suspension | |
|---|---|
| 7-Chloro-4-[1-(2-fluorophenyl)ethoxy]quinoline | 12.5% |
| "MAKON 10" (10 moles ethylene oxide nonylphenol surfactant) | 1.0% |
| "ZEOSYL 200" (silica) | 1.0% |
| "AF-100" (silicon based antifoam agent) | 0.2% |
| "POLYFON H" (lignosulfonate dispersing agent) | 0.2% |
| 2% xanthan gum solution | 10.0% |
| tap water | 75.1% |

We claim:
1. A fungicidal method which comprises applying to the locus of a plant pathogen a disease inhibiting and phytologically acceptable amount of a compound of formula (1)

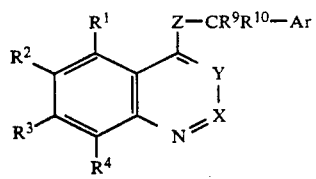

wherein
$R^1$ to $R^4$ are independently:
H, halo, $(C_1-C_4)$ alkyl, branched $(C_3-C_4)$ alkyl, halo $(C_1-C_4)$ alkyl, $(C_1-C_4)$ alkoxy, halo $(C_1-C_4)$ alkoxy, $NO_2$, or $NH_2$, at least two of $R^1$ to $R^4$ being H, both X and Y are $CR^5$,
$R^5$ is H, $CH_3$, or Cl;
Z is O, $NR^6$, or $CR^7R^8$;
$R^6$ is H, $(C_1-C_4)$ alkyl, or $(C_2-C_4)$ acyl,
$R^7$ and $R^9$ are independently H, $(C_1-C_4)$ alkyl, branched $(C_3-C_4)$ alkyl, or $(C_1-C_4)$ acyl, or $R^7$ and $R^8$ combine to form a saturated or unsaturated carbocyclic ring containing three to seven carbon atoms, or one or both of $R^7$ and $R^8$ can combine with one or both of $R^9$ and $R^{10}$ to form a multiple bond;
$R^9$ and $R^{10}$ are independently H, $(C_1-C_3)$ alkyl, phenyl, substituted phenyl, $(C_3-C_8)$ cycloalkyl, hydroy, halo, or acetyl, or $R^9$ and $R^{10}$ combine to form a saturated or unsaturated carbocyclic ring containing three to seven carbon atoms; and Ar is
$(C_3-C_8)$ cycloalkyl,
substituted $(C_3-C_8)$ cycloalkyl,
$(C_3-C_8)$ cycloalkenyl,
naphthyl,
dihydronaphthyl,
tetrahydronaphthyl,
decahydronaphthyl,
1,3-benzodioxolyl,
fluorenyl,
pyridyl
substituted pyridyl,
2,3-dihydro-1,4-benzodioin-2-yl,
furyl optionally substituted with halo, $CF_3$, CN, $NO_2$, $(C_1-C_4)$ alkyl, branched $(C_3-C_4)$ alkyl, phenyl, or $(C_1-C_4)$ alkoxy,
thienyl optionally substituted with halo, $CF_3$, CN, $NO_2$, $(C_1-C_4)$ alkyl, branched $(C_3-C_4)$ alkyl, phenyl, or $(C_1-C_4)$ alkoxy,
a group of the formula (2) or (2a)

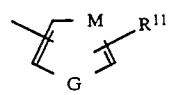

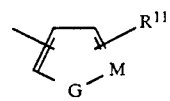

wherein $R^{11}$ is H, halo, $CF_3$, CN, $NO_2$, $(C_1-C_4)$ alkyl, branched $(C_3-C_4)$ alkyl, phenyl, or $(C_1-C_4)$ alkoxy, M is N or CH and G is O, $NR^{20}$, or $CH_2$, provided that M is N or G is $NR^{20}$, where $R^{20}$ is H, $(C_1-C_4)$ alkyl, $(C_1-C_4)$ acyl, phenylsulfonyl, or substituted phenylsulfonyl;
a group of the formula (3)

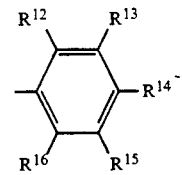

wherein
$R^{12}$ to $R^{16}$ are independently H, halo, $(C_1-C_{10})$ alkyl, branched $(C_3-C_6)$ alkyl, halo $(C_1-C_7)$ alkyl, $(C_1-C_7)$ alkoxy, halo $(C_1-C_7)$ alkoxy, phenoxy, substituted phenoxy, phenyl, substituted phenyl, phenylthio, or substituted phenylthio, $NO_2$, $NH_2$, acetoxy, OH, CN, or $SiR^{17}R^{18}R^{19}$, or $OSiR^{17}R^{18}R^{19}$, where $R^{17}$, $R^{18}$, or $R^{19}$ are independently $C_1-C_4$ alkyl, $C_1-C_4$ branched alkyl, phenyl, or substituted phenyl, provided that unless each of $R^{12}$ to $R^{16}$ is F, $CH_3$, or H, then at least two of $R^{12}$ to $R^{16}$ are H;

or an acid addition salt of a compound of formula (1), or an N-oxide of a compound of formula (1);

wherein, as used above, the term "substituted phenyl" refers to phenyl substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted phenoxy" refers to phenoxy substituted with up to three groups independently selected from halo, $(C_1-C_{10})$ alkyl, branched $(C_3-C_6)$ alkyl, halo $(C_1-C_7)$ alkyl, hydroxy $(C_1-C^7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted phenylthio" refers to phenylthio substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ halo $(C_1-C_7)$ alkoxy, phenoxy, phenyl, $NO_2$, OH, CN, $(C_1-C_4)$ alkanoyloxy, or benzoyloxy;

"substituted phenylsulfonyl" refers to phenylsulfonyl substituted with up to three groups independently selected from halo, $(C_1-C_{10})$ alkyl, branched $(C_3-C_6)$ alkyl, halo $(C_1-C_7)$ alkyl, hydroy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted $(C_3-C_8)$ cycloalkyl" refers to a $(C_3-C_8)$ cycloalkyl group substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy; and "substituted pyridyl" refers to a pyridyl group substituted with halo, halomethyl, CN, $NO_2$, $(C_1-C_4)$ alkyl, $(C_3-C_4)$ branched alkyl, phenyl, $(C_1-C_7)$ alkoxy, or halo $(C_1-C_7)$ alkoxy;

provided that

Ar is not 5-nitro-2-furyl.

2. A compound formula

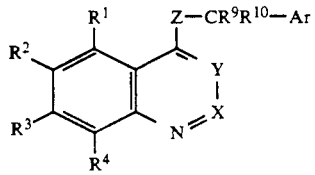

(1)

wherein $R^1$ to $R^4$ are independently:

H, halo, $(C_1-C_4)$ alkyl, branched $(C_3-C_4)$ alkyl, halo $(C_1-C_4)$ alkyl, $(C_1-C_4)$ alkoxy, halo $(C_1-C_4)$ alkoxy, $NO_2$, or $NH_2$, at least two of $R^1$ to $R^4$ being H, both X and Y are $CR^5$, $R^5$ is H, $CH_3$, or Cl;

Z is O, $NR^6$, or $CR^7R^8$;

$R^6$ is H, $(C_1-C_4)$ alkyl, or $(C_2-C_4)$ acyl, $R^7$ and $R^8$ are independently H, $(C_1-C_4)$ alkyl, branched $(C_3-C_4)$ alkyl, or $(C_1-C_4)$ acyl, or $R^7$ and $R^8$ combine to form a saturated or unsatured carbocyclic ring containing three to seven carbon atoms, or one or both of $R^7$ and $R^8$ can combine with one or both of $R^9$ and $R^{10}$ to form a multiple bond;

$R^9$ and $R^{10}$ are independently H, $(C_1-C_3)$ alkyl, phenyl, substituted phenyl, $(C_3-C_8)$ cycloalkyl, hydroy, halo, or acetyl, or $R^9$ and $R^{10}$ combine to form a saturated or unsaturated carbocyclic ring containing three to seven carbon atoms; and Ar is $(C_3-C_8)$ cycloalkyl, substituted $(C_3-C_8)$ cycloalkyl, $(C_3-C_8)$ cycloalkenyl, naphthyl, dihydronaphthyl, tetrahydronaphthyl, decahydronaphthyl, 1,3-benzodioxolyl, fluorenyl, pyridyl substituted pyridyl, 2,3-dihydro-1,4-benzodioin-2-yl, furyl optionally substituted with halo, $CF_3$, CN, $NO_2$, $(C_1-C_4)$ alkyl, branched $(C_3-C_4)$ alkyl, phenyl, or $(C_1-C_4)$ alkoy, thienyl optionally substituted with halo, $CF_3$, CN, $NO_2$, $(C_1-C_4)$ alkyl, branched $(C_3-C_4)$ alkyl, phenyl, or $(C_1-C_4)$ alkoxy, a group of the formula (2) or (2a)

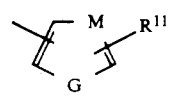

(2)

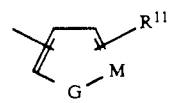

(2a)

wherein $R^{11}$ is H, halo, $CF_3$, CN, $NO_2$, $(C_1-C_4)$ alkyl, branched $(C_3-C_4)$ alkyl, phenyl, or $(C_1-C_4)$ alkoxy, M is N or CH and G is O, $NR^{20}$, or $CH_2$, provided that M is N or G is $NR^{20}$, where $R^{20}$ is H, $(C_1-C_4)$ alkyl, $(C_1-C_4)$ acyl, phenylsulfonyl, or substituted phenylsulfonyl;

a group of the formula (3)

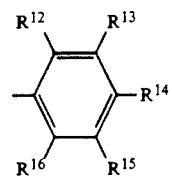

(3)

wherein $R^{12}$ to $R^{16}$ are independently H, halo, $(C_1-C_{10})$ alkyl, branched $(C_3-C_6)$ alkyl, halo $(C_1-C_7)$ alkyl, $(C_1-C_7)$ alkoxy, halo $(C_1-C_7)$ alkoxy, phenoxy, substituted phenoxy, phenyl, substituted phenyl, phenylthio, or substituted phenylthio, $NO_2$, $NH_2$, acetoy, OH, CN, or $SiR^{17}R^{18}R^{19}$, or $OSiR^{17}R^{18}R^{19}$, where $R^{17}$, $R^{18}$, or $R^{19}$ are independently $C_1-C_4$ alkyl, $C_1-C_4$ branched alkyl, phenyl, or substituted phenyl, provided that unless each of $R^{12}$ to $R^{16}$ is F, $CH_3$, or H, then at least two of $R^{12}$ to $R^{16}$ are H;

or an acid addition salt of a compound of formula (1), or an N-oxide of a compound of formula (1) where Y is $CR^5$;

wherein, as used above, the term "substituted phenyl" refers to phenyl substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted phenoxy" refers to phenoxy substituted with up to three groups independently selected from halo, $(C_1-C_{10})$ alkyl, branched $(C_3-C_6)$ alkyl, halo $(C_1-C_7)$ alkyl, hydroxy $(C_1-C^7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted phenylthio" refers to phenylthio substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ halo $(C_1-C_7)$ alkoxy, phenoxy, phenyl, $NO_2$, OH, CN, $(C_1-C_4)$ alkanoyloxy, or benzoyloxy;

"substituted phenylsulfonyl" refers to phenylsulfonyl substituted with up to three groups independently selected from halo, $(C_1-C_{10})$ alkyl, branched $(C_3-C_6)$ alkyl, halo $(C_1-C_7)$ alkyl, hydroy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted $(C_3-C_8)$ cycloalkyl" refers to a $(C_3-C_8)$ cycloalkyl group substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy; and "substituted pyridyl" refers to a pyridyl group substituted with halo, halomethyl, CN, $NO_2$, $(C_1-C_4)$ alkyl, $(C_3-C_4)$ branched alkyl, phenyl, $(C_1-C_7)$ alkoxy, or halo $(C_1-C_7)$ alkoxy;

provided that if X and Y are $CR^5$ and Z is $NR^6$, then $R^4$ is Cl or F, or Ar is a group of formula (3) wherein one of $R^{12}$ to $R^{16}$ is substituted phenyl, phenoxy, substituted phenoxy, phenylthio, substituted phenylthio, halo $(C_1-C_4)$alkyl, or halo $(C_1-C_4)$ alkoxy, Ar is not 5-nitro-2-furyl.

provided further that 4-benzoxyquinoine and its N-oxide are excluded.

3. A compound of claim 2 wherein X and Y are $CR^5$, Z is O, $R^9$ and $R^{10}$ independently H, $(C_1-C_3)$ alkyl phenyl, substituted phenyl, $(C_3-C_8)$ cycloalkyl, hydroxy, halo, or acetyl; and Ar is a group of formula (3) wherein $R^{12}$ to $R^{16}$ are independently H, halo, I, $(C_1-C_{10})$ alkyl, branched $(C_3-C_6)$ alkyl, halo $(C_1-C_7)$ alkyl, $(C_1-C_7)$ alkoxy, or halo $(C_1-C_7)$ alkoxy.

4. A compound of formula (1)

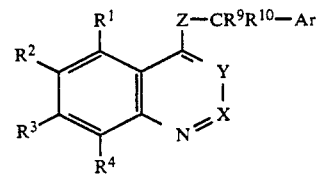

wherein $R^1$ to $R^4$ are independently:

H, halo, $(C_1-C_4)$ alkyl, branched $(C_3-C_4)$ alkyl, halo $(C_1-C_4)$ alkyl, $(C_1-C_4)$ alkoxy, halo $(C_1-C_4)$ alkoxy, $NO_2$, or $NH_2$, at least two of $R^1$ to $R^4$ being H, X and Y are $CR^5$, $R^5$ is H, $CH_3$, or Cl;

Z is O, $NR^6$, or $CR^7R^8$;

$R^6$ is H, $(C_1-C_4)$ alkyl, or $(C_2-C_4)$ acyl, $R^7$ and $R^8$ are independently H, $(C_1-C_4)$ alkyl, branched $(C_3-C_4)$ alkyl, or $(C_1-C_4)$ acyl, or $R^7$ and $R^8$ combine to form a saturated or unsatured carbocyclic ring containing three to seven carbon atoms, or one or both of $R^7$ and $R^8$ can combine with one or both of $R^9$ and $R^{10}$ to form a multiple bond;

$R^9$ and $R^{10}$ are independently H, $(C_1-C_3)$ alkyl, phenyl, substituted phenyl, $(C_3-C_8)$ cycloalkyl, hydroy, halo, or acetyl, or $R^9$ and $R^{10}$ combine to form a saturated or unsaturated carbocyclic ring containing three to seven carbon atoms; and Ar is $(C_3-C_8)$ cycloalkyl, substituted $(C_3-C_8)$ cycloalkyl, $(C_3-C_8)$ cycloalkenyl, naphthyl, dihydronaphthyl, tetrahydronaphthyl, decahydronaphthyl, 1,3-benzodioxolyl, fluorenyl, pyridyl substituted pyridyl, 2,3-dihydro-1,4-benzodioin-2-yl, furyl optionally substituted with halo, $CF_3$, CN, $NO_2$, $(C_1-C_4)$ alkyl, branched $(C_3-C_4)$ alkyl, phenyl, or $(C_1-C_4)$ alkoy, thienyl optionally substituted with halo, $CF_3$, CN, $NO_2$, $(C_1-C_4)$ alkyl, branched $(C_3-C_4)$ alkyl, phenyl, or $(C_1-C_4)$ alkoxy, a group of the formula (2) or (2a)

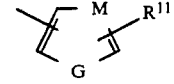

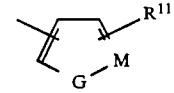

wherein $R^{11}$ is H, halo, $CF_3$, CN, $NO_2$, $(C_1-C_4)$ alkyl, branched $(C_3-C_4)$ alkyl, phenyl, or $(C_1-C_4)$ alkoxy, M is N or CH and G is O, $NR^{20}$, or $CH_2$, provided that M is N or G is $NR^{20}$, where $R^{20}$ is H, $(C_1-C_4)$ alkyl, $(C_1-C_4)$ acyl, phenylsulfonyl, or substituted phenylsulfonyl;

a group of the formula (3)

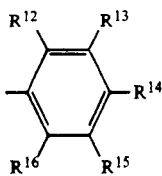

(3)

wherein $R^{12}$ to $R^{16}$ are independently H, halo, $(C_1-C_{10})$ alkyl, branched $(C_3-C_6)$ alkyl, halo $(C_1-C_7)$ alkyl, $(C_1-C_7)$ alkoxy, halo $(C_1-C_7)$ alkoxy, phenoxy, substituted phenoxy, phenyl, substituted phenyl, phenylthio, or substituted phenylthio, $NO_2$, $NH_2$, acetoxy, OH, CN, or $SiR^{17}R^{18}R^{19}$, or $OSiR^{17}R^{18}R^{19}$, where $R^{17}$, $R^{18}$, or $R^{19}$ are independently $C_1-C_4$ alkyl, $C_1-C_4$ branched alkyl, phenyl, or substituted phenyl, provided that unless each of $R^{12}$ to $R^{16}$ is F, $CH_3$, or H, then at least two of $R^{12}$ to $R^{16}$ are H;

or an acid addition salt of a compound of formula (1), or an N-oxide of a compound of formula (1), wherein, as used above, the term "substituted phenyl" refers to phenyl substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted phenoxy" refers to phenoxy substituted with up to three groups independently selected from halo, $(C_1-C_{10})$ alkyl, branched $(C_3-C_6)$ alkyl, halo $(C_1-C_7)$ alkyl, hydroxy $(C_1-C^7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted phenylthio" refers to phenylthio substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ halo $(C_1-C_7)$ alkoxy, phenoxy, phenyl, $NO_2$, OH, CN, $(C_1-C_4)$ alkanoyloxy, or benzoyloxy;

"substituted phenylsulfonyl" refers to phenylsulfonyl substituted with up to three groups independently selected from halo, $(C_1-C_{10})$ alkyl, branched $(C_3-C_6)$ alkyl, halo $(C_1-C_7)$ alkyl, hydroy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy;

"substituted $(C_3-C_8)$ cycloalkyl" refers to a $(C_3-C_8)$ cycloalkyl group substituted with up to three groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzoyloxy; and "substituted pyridyl" refers to a pyridyl group substituted with halo, halomethyl, CN, $NO_2$, $(C_1-C_4)$ alkyl, $(C_3-C_4)$ branched alkyl, phenyl, $(C_1-C_7)$ alkoxy, or halo $(C_1-C_7)$ alkoxy;

provided that if X and Y are $CR^5$ and Z is $NR^6$, then $R^4$ is Cl or F, or Ar is a group of formula (3) wherein one of $R^{12}$ to $R^{16}$ is substituted phenyl, phenoxy, substituted phenoxy, phenylthio, substituted phenylthio, halo $(C_1-C_4)$alkyl, or halo $(C_1-C_4)$ alkoxy, Ar is not 5-nitro-2-furyl.

at least one of the following conditions is satisfied:

(1) Z is $CR^7R^8$;

(2) $R^3$ is Cl and $R^1$, $R^2$, and $R^4$ are H;

(3) $R^9$ is $CH_3$ and $R^{10}$ is H;

(4) Ar is a group of formula (3) wherein at least one of $R^{12}$ to $R^{16}$ is F;

(5) Ar is a group of formula (3) wherein at least one of $R^{12}$ to $R^{16}$ is $CF_3$;

(6) Ar is a group of formula (3) wherein at least one of $R^{12}$ to $R^{16}$ is $(C_1-C_4$ alkoxy);

(7) Ar is a group of formula (3) wherein at least one of $R^{12}$ to $R^{16}$ is halo $(C_1-C_4$ alkoxy).

5. A compound of claim 4 wherein X and Y are CH.

6. A compound of claim 4 wherein Z is O.

7. A compound of claim 4 wherein Z is $NR^6$.

8. A compound of claim 4 wherein Z is $CR^7R^8$.

9. A compound of claim 4 wherein $R^3$ is Cl and $R^1$, $R^2$, and $R^4$ are H.

10. A compound of claim 4 wherein Ar is a group of formula (3) wherein at least one of $R^{12}$ to $R^{16}$ is F.

11. A compound of claim 4 wherein Ar is a group of formula (3) wherein at least one of $R^{12}$ to $R^{16}$ is $CF_3$.

12. A compound of claim 4 which is 7-chloro-4-[1-(4-fluorophenyl)ethoxy]quinoline.

13. The compound of claim 4 which is 7-chloro-4-[1-(2-fluorophenyl)quinoline.

14. The compound of claim 4 which is 7-chloro-4-[1-(3-fluorophenyl)ethoxy]quinoline.

15. The compound of claim 4 which is (S)-7-chloro-4-[1-(2-fluorophenyl)ethoxy]quinoline.

16. The compound of claim 4 which is (R)-7-chloro-4-[1-(2-fluorophenyl)ethoxy]quinoline.

17. The compound of claim 4 which is N-[(4-chlorophenyl)methyl]-8-fluoro-4-quinolinamine.

18. The compound of claim 4 which is N-[1-(4-chlorophenyl)ethyl[-8-fluoro-4-quinolinamine.

19. A compound of claim 2 wherein $R^9$ is $CH_3$ and $R^{10}$ is H.

20. A compound of claim 2 wherein Ar is a group of formula (3) wherein at least one of $R^{12}$ to $R^{16}$ is $(C_1-C_4)$ alkoxy.

21. A compound of claim 2 wherein Ar is a group of formula (3) wherein at least one of $R^{12}$ to $R^{16}$ is halo $(C_1-C_4)$ alkoxy.

22. A compound of claim 21 wherein at least one of $R^{12}$ to $R^{16}$ is trifluoromethoxy.

23. A fungicidal method which comprises applying to the locus of a plant pathogen a disease inhibiting and phytologically acceptable amount of a compound of claim 4.

24. A fungicidal composition which comprises a compound of formula (1) as defined in claim 4 in combination with a phytologically-acceptable carrier.

* * * * *